(12) United States Patent
Van Der Schaar et al.

(10) Patent No.: US 10,073,357 B2
(45) Date of Patent: Sep. 11, 2018

(54) MEASURING A PROCESS PARAMETER FOR A MANUFACTURING PROCESS INVOLVING LITHOGRAPHY

(71) Applicant: ASML Netherlands B.V., Veldhoven (NL)

(72) Inventors: Maurits Van Der Schaar, Veldhoven (NL); Arie Jeffrey Den Boef, Veldhoven (NL); Omer Abubaker Omer Adam, Veldhoven (NL); Te-Chih Huang, Veldhoven (NL); Youping Zhang, Santa Clara, CA (US)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/117,409

(22) PCT Filed: Jan. 28, 2015

(86) PCT No.: PCT/EP2015/051680
§ 371 (c)(1),
(2) Date: Aug. 8, 2016

(87) PCT Pub. No.: WO2015/124391
PCT Pub. Date: Aug. 27, 2015

(65) Prior Publication Data
US 2016/0349627 A1 Dec. 1, 2016

Related U.S. Application Data

(60) Provisional application No. 61/943,160, filed on Feb. 21, 2014.

(51) Int. Cl.
*G01B 11/00* (2006.01)
*G03B 27/32* (2006.01)
(Continued)

(52) U.S. Cl.
CPC ......... *G03F 7/70633* (2013.01); *G01N 21/47* (2013.01); *G01N 21/8806* (2013.01); *G03F 7/70683* (2013.01); *G01N 2201/12* (2013.01)

(58) Field of Classification Search
CPC ............... G01N 21/47; G01N 21/8806; G01N 2201/12; G03F 7/70633; G03F 7/70683
(Continued)

(56) References Cited

U.S. PATENT DOCUMENTS 7,587,704 B2 9/2009 Ye et al.
2006/0066855 A1 3/2006 Boef et al.
(Continued)

OTHER PUBLICATIONS

International Search Report and Written Opinion of the International Searching Authority directed to related International Patent Application No. PCT/EP2015/051680, dated Jun. 12, 2015; 8 pages.
(Continued)

*Primary Examiner* — Colin Kreutzer
(74) *Attorney, Agent, or Firm* — Sterne, Kessler, Goldstein & Fox P.L.L.C.

(57) ABSTRACT

There is disclosed a method of measuring a process parameter for a manufacturing process involving lithography. In a disclosed arrangement the method comprises performing first and second measurements of overlay error in a region on a substrate, and obtaining a measure of the process parameter based on the first and second measurements of overlay error. The first measurement of overlay error is designed to be more sensitive to a perturbation in the process parameter than the second measurement of overlay error by a known amount.

13 Claims, 6 Drawing Sheets

(51) Int. Cl.
*G03B 27/74* (2006.01)
*G03F 7/20* (2006.01)
*G01N 21/47* (2006.01)
*G01N 21/88* (2006.01)

(58) Field of Classification Search
USPC .................. 355/67, 68, 77; 356/399–401
See application file for complete search history.

(56) References Cited

U.S. PATENT DOCUMENTS

2013/0035888 A1   2/2013  Kandel et al.
2013/0054186 A1   2/2013  Den Boef
2013/0162996 A1   6/2013  Straaijer et al.
2013/0308142 A1  11/2013  Straaijer

OTHER PUBLICATIONS

International Preliminary Report on Patentability directed to related International Patent Application No. PCT/EP2015/051680, dated Aug. 23, 2016; 6 pages.

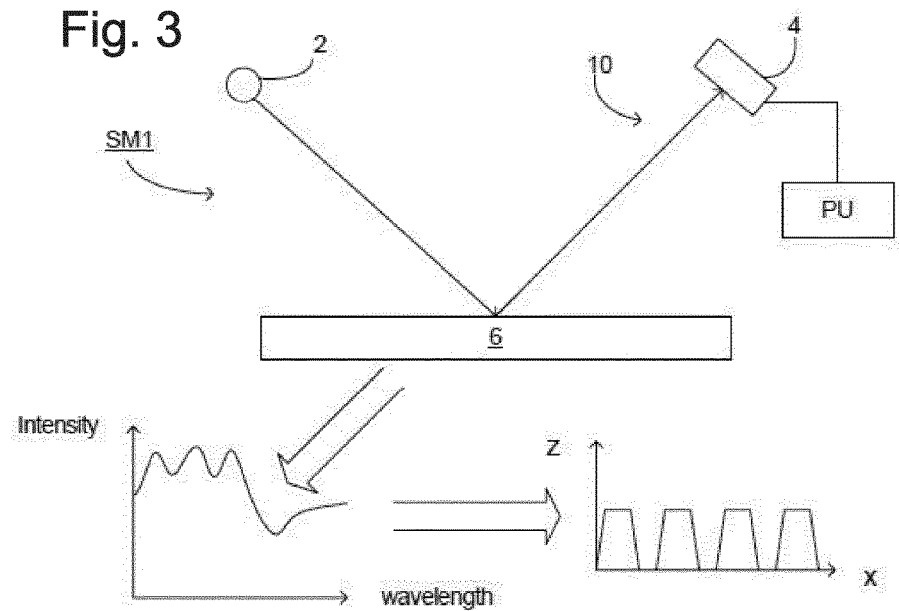
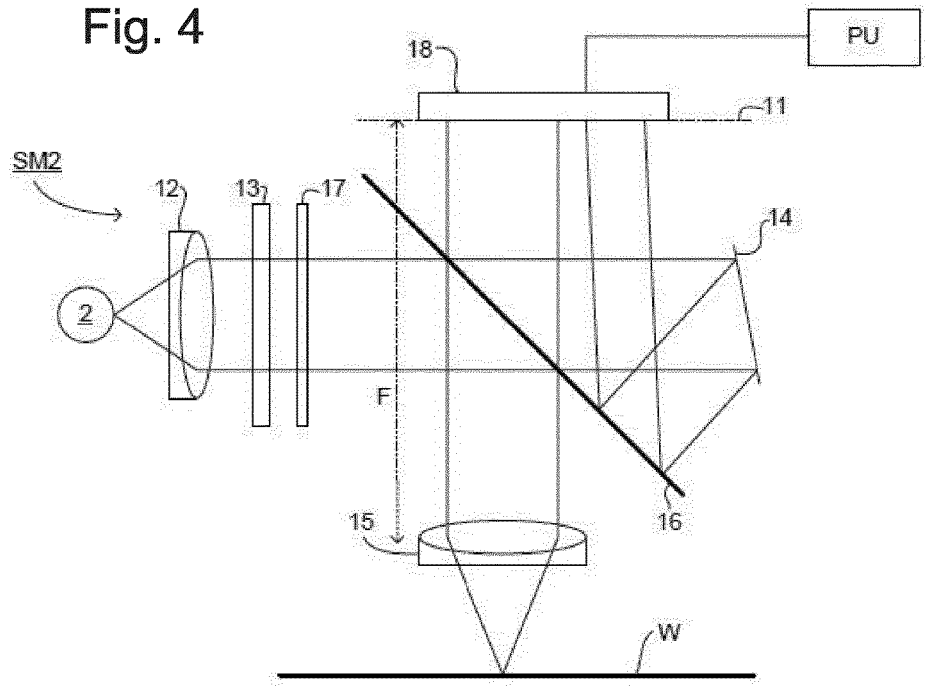

MEASURING A PROCESS PARAMETER FOR A MANUFACTURING PROCESS INVOLVING LITHOGRAPHY

CROSS-REFERENCE TO RELATED APPLICATIONS

This application claims the benefit of U.S. provisional application 61/943,160, which was filed on Feb. 21, 2014 and which is incorporated herein in its entirety by reference.

FIELD

The present description relates to methods and apparatus for measuring a process parameter for a manufacturing process involving lithography, particularly a feature asymmetry such as a side-wall angle unbalance or a tilt in the floor of a trench.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable to frequently make measurements of the structures created, e.g., for process control and verification. One or more parameters of the structures are typically measured or determined, for example the overlay error between successive layers formed in or on the substrate. There are various techniques for making measurements of the microscopic structures formed in a lithographic process. Various tools for making such measurements are known, including scanning electron microscopes, which are often used to measure critical dimension (CD), and specialized tools to measure overlay, the accuracy of alignment of two layers in a device. An example of such a tool is a scatterometer developed for use in the lithographic field. This device directs a beam of radiation onto a target on the surface of the substrate and measures one or more properties of the redirected radiation—e.g., intensity at a single angle of reflection as a function of wavelength; intensity at one or more wavelengths as a function of reflected angle; or polarization as a function of reflected angle—to obtain a set of data from which a property of interest of the target can be determined. Determination of the property of interest may be performed by various techniques: e.g., reconstruction of the target structure by iterative approaches such as rigorous coupled wave analysis or finite element methods, library searches, and principal component analysis.

SUMMARY

While overlay errors can be measured relatively quickly and efficiently, measurements of certain process parameters such as side-wall asymmetries can be much more time-consuming and/or involve damage to the substrate being inspected.

It is desirable, for example, to allow measurements of such process parameters to be performed more efficiently.

In an embodiment, there is provided a method of measuring a process parameter for a manufacturing process involving lithography comprising performing first and second measurements of overlay error in a region on a substrate and obtaining a measure of the process parameter based on the first and second measurements of overlay error. The first measurement of overlay error is designed to be more sensitive to a perturbation in the process parameter than the second measurement of overlay error by a known amount.

In another embodiment, there is provided an inspection apparatus for measuring a process parameter for a manufacturing process involving lithography. It includes an optical system arranged to direct radiation onto a substrate. A detector arranged to detect radiation after interaction between the radiation and the substrate. An overlay error processing module arranged to obtain a measure of overlay error by analyzing an output from the detector. A process parameter obtaining module arranged to obtain a measure of the process parameter by causing the optical system, detector and overlay error processing module to: perform first and second measurements of overlay error in a region on the substrate, and obtain a measure of the process parameter based on the first and second measurements of overlay error. The first measurement of overlay error is designed to be more sensitive to a perturbation in the process parameter than the second measurement of overlay error by a known amount.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the relevant art(s) to make and use the invention.

Embodiments will now be described, by way of example only, with reference to the accompanying drawings in which:

FIG. 3 schematically depicts an embodiment of a scatterometer;

FIG. 4 schematically depicts a further embodiment of a scatterometer;

Figure 1:
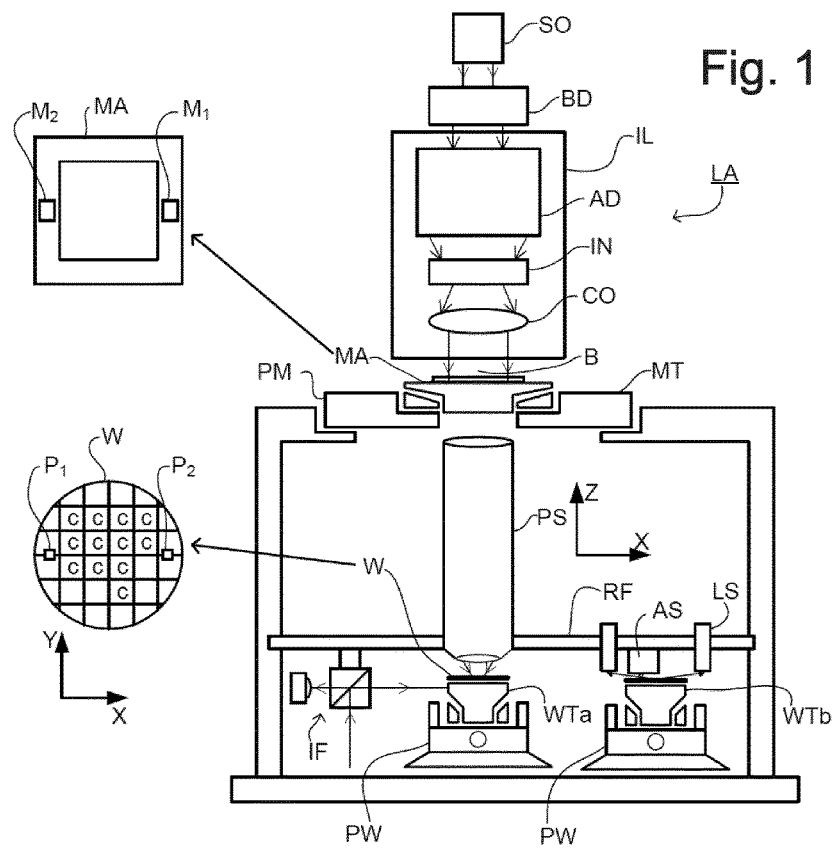
FIG. 1 schematically depicts an embodiment of a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals, and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically shows a lithographic apparatus LAP including a source collector module SO according to an embodiment of the invention. The apparatus comprises: an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support structure holds the patterning device in a manner that depends on the orientation of the patterning device, the design of the lithographic apparatus, and other conditions, such as for example whether or not the patterning device is held in a vacuum environment. The patterning device support structure can use mechanical, vacuum, electrostatic or other clamping techniques to hold the patterning device. The patterning device support structure may be a frame or a table, for example, which may be fixed or movable as required. The patterning device support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more tables (e.g., two or more substrate table, two or more patterning device support structures, or a substrate table and metrology table). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WTa may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two tables WTa, WTb (e.g., two substrate tables) and two stations—an exposure station and a measurement station—between which the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

Figure 2:
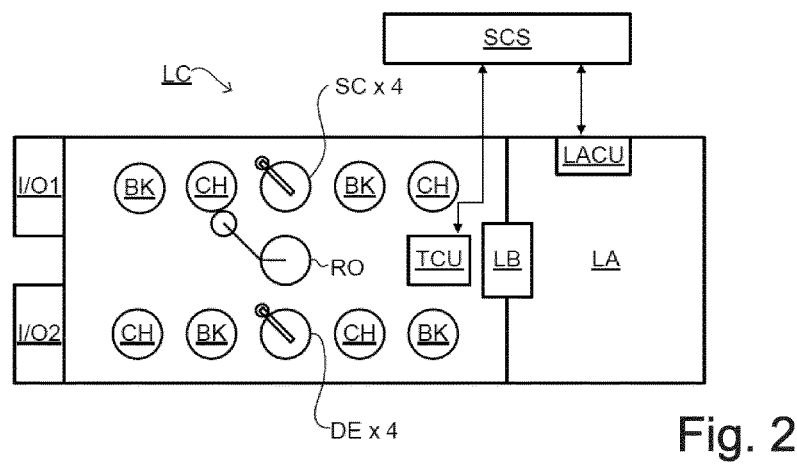
FIG. 2 schematically depicts an embodiment of a lithographic cell or cluster.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties. These properties may include overlay error between subsequent layers, line thickness, critical dimension (CD), etc. Additionally, as described below, the inspection may be used to derive process parameters such as side-wall angle unbalance. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

FIG. 3 depicts an embodiment of a scatterometer SM1. It comprises a broadband (white light) radiation projector 2 which projects radiation onto a substrate 6. The reflected radiation is passed to a spectrometer detector 4, which measures a spectrum 10 (i.e. a measurement of intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another embodiment of a scatterometer SM2 is shown in FIG. 4. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), desirably at least 0.9 or at least 0.95. An immersion scatterometer may even have a lens with a numerical aperture over 1. The reflected radiation then transmits through partially reflective surface 16 into a detector 18 in order to have the scatter spectrum detected. The detector may be located in the back-projected pupil plane 11, which is at the focal length of the lens 15, however the pupil plane may instead be re-imaged with auxiliary optics (not shown) onto the detector 18. The pupil plane is the plane in which the radial position of radiation defines the angle of incidence and the angular position defines the azimuth angle of the radiation. The detector is desirably a two-dimensional detector so that a two-dimensional angular scatter spectrum (i.e. a measurement of intensity as a function of angle of scatter) of the substrate target can be measured. The detector 18 may be, for example, an array of CCD or CMOS sensors, and may have an integration time of, for example, 40 milliseconds per frame.

A reference beam is often used, for example, to measure the intensity of the incident radiation. To do this, when the radiation beam is incident on the partially reflective surface 16 part of it is transmitted through the surface as a reference beam towards a reference mirror 14. The reference beam is then projected onto a different part of the same detector 18.

One or more interference filters 13 are available to select a wavelength of interest in the range of, say, 405-790 nm or even lower, such as 200-300 nm. The interference filter(s) may be tunable rather than comprising a set of different filters. A grating could be used instead of or in addition to one or more interference filters.

The detector 18 may measure the intensity of scattered radiation at a single wavelength (or narrow wavelength range), the intensity separately at multiple wavelengths or the intensity integrated over a wavelength range. Further, the detector may separately measure the intensity of transverse magnetic—(TM) and transverse electric—(TE) polarized radiation and/or the phase difference between the transverse magnetic- and transverse electric-polarized radiation.

Using a broadband radiation source 2 (i.e. one with a wide range of radiation frequencies or wavelengths—and therefore of colors) is possible, which gives a large etendue, allowing the mixing of multiple wavelengths. The plurality of wavelengths in the broadband desirably each has a bandwidth of δλ and a spacing of at least 2δλ (i.e. twice the wavelength bandwidth). Several different portions of an extended radiation source which have been split using, e.g., fiber bundles may be considered as individual sources. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in U.S. patent application publication no. US 2006-0066855, which document is hereby incorporated in its entirety by reference.

By comparing one or more properties of the beam before and after it has been redirected by the target, one or more properties of the substrate may be determined. This may be done, for example, by comparing the redirected beam with theoretical redirected beams calculated using a model of the substrate and searching for the model that gives the best fit between measured and calculated redirected beams. Typically a parameterized generic model is used and the parameters of the model, for example width, height and sidewall angle of the pattern, are varied until the best match is obtained.

Two main types of scatterometer are used. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity (or intensity ratio and phase difference in case of an ellipsometric configuration) of the scattered radiation as a function of angle. Alternatively, measurement signals of different wavelengths may be measured separately and combined at an analysis stage. Polarized radiation may be used to generate more than one spectrum from the same substrate.

In order to determine one or more parameters of the substrate, a best match is typically found between the theoretical spectrum produced from a model of the substrate and the measured spectrum produced by the redirected beam as a function of either wavelength (spectroscopic scatterometer) or angle (angularly resolved scatterometer). To find the best match there are various methods, which may be combined. For example, a first method is an iterative search method, where a first set of model parameters is used to calculate a first spectrum, a comparison being made with the measured spectrum. Then a second set of model parameters is selected, a second spectrum is calculated and a comparison of the second spectrum is made with the measured spectrum. These steps are repeated with the goal of finding the set of parameters that gives the best matching spectrum. Typically, the information from the comparison is used to steer the selection of the subsequent set of parameters. This process is known as an iterative search technique. The model with the set of parameters that gives the best match is considered to be the best description of the measured substrate.

A second method is to make a library of spectra, each spectrum corresponding to a specific set of model parameters. Typically the sets of model parameters are chosen to cover all or almost all possible variations of substrate properties. The measured spectrum is compared to the spectra in the library. Similarly to the iterative search method, the model with the set of parameters corresponding to the spectrum that gives the best match is considered to be the best description of the measured substrate. Interpolation techniques may be used to determine more accurately the best set of parameters in this library search technique.

In any method, sufficient data points (wavelengths and/or angles) in the calculated spectrum should be used in order to enable an accurate match, typically between 80 up to 800 data points or more for each spectrum. Using an iterative method, each iteration for each parameter value would involve calculation at 80 or more data points. This is multiplied by the number of iterations needed to obtain the correct profile parameters. Thus many calculations may be required. In practice this leads to a compromise between accuracy and speed of processing. In the library approach, there is a similar compromise between accuracy and the time required to set up the library.

In any of the scatterometers described above, the target on substrate W may be a grating which is printed such that after development, the bars are formed of solid resist lines. The bars may alternatively be etched into the substrate. The target pattern is chosen to be sensitive to a parameter of interest, such as focus, dose, overlay, chromatic aberration in the lithographic projection apparatus, etc., such that variation in the relevant parameter will manifest as variation in the printed target. Accordingly, the scatterometry data of the printed target pattern is used to reconstruct the target pattern. The parameters of the target pattern, such as line width and shape, may be input to the reconstruction process, performed by a processing unit PU, from knowledge of the printing step and/or other scatterometry processes.

While embodiments of a scatterometer have been described herein, other types of metrology apparatus may be used in an embodiment. For example, a dark field metrology apparatus such as described in U.S. Patent Application Publication No. 2013-0308142, which is incorporated herein in its entirety by reference, may be used. Further, those other types of metrology apparatus may use a completely different technique than scatterometry.

Figure 5:
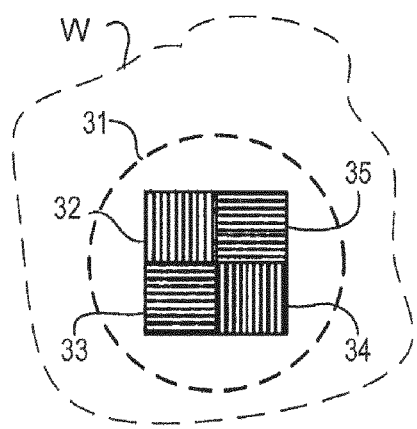
FIG. 5 schematically depicts a form of multiple grating target and an outline of a measurement spot on a substrate.

FIG. 5 depicts an example composite metrology target formed on a substrate according to known practice. The composite target comprises four gratings 32, 33, 34, 35 positioned closely together so that they will all be within a measurement spot 31 formed by the illumination beam of the metrology apparatus. The four targets thus are all simultaneously illuminated and simultaneously imaged on sensor 4, 18. In an example dedicated to overlay measurement, gratings 32, 33, 34, 35 are themselves composite gratings formed by overlying gratings that are patterned in different layers of the semi-conductor device formed on substrate W. Gratings 32, 33, 34, 35 may have differently biased overlay offsets in order to facilitate measurement of overlay between the layers in which the different parts of the composite gratings are formed. Gratings 32, 33, 34, 35 may also differ in their orientation, as shown, so as to diffract incoming radiation in X and Y directions. In one example, gratings 32 and 34 are X-direction gratings with biases of +d, −d, respectively. This means that grating 32 has its overlying components arranged so that if they were both printed exactly at their nominal locations, one of the components would be offset relative to the other by a distance d. Grating 34 has its components arranged so that if perfectly printed there would be an offset of d, but in the opposite direction to the first grating and so on. Gratings 33 and 35 may be Y-direction gratings with offsets +d and −d respectively. While four gratings are illustrated, another embodiment may include a larger matrix to obtain desired accuracy. For example, a 3×3 array of nine composite gratings may have biases −4d, −3d, −2d, −d, 0, +d, +2d, +3d, +4d. Separate images of these gratings can be identified in the image captured by sensor 4, 18.

The metrology targets as described herein may be, for example, overlay targets designed for use with a metrology tool such as Yieldstar stand-alone or integrated metrology tool, and/or alignment targets such as those typically used with a TwinScan lithographic system, both available from ASML.

In general, metrology targets for use with such systems should be printed on the substrate with dimensions that meet the design specification for the particular microelectronic device to be imaged on that substrate. As processes continue to push against the limits of lithographic device imaging resolution in advanced process nodes, the design rule and process compatibility requirements place stress on the selection of appropriate targets. As the targets themselves become more advanced, often requiring the use of resolution enhancement technology, such as phase-shift patterning devices, and optical proximity correction, the printability of the target within the process design rules becomes less certain. As a result, proposed metrology target design may be subject to testing and/or simulation in order to confirm their suitability and/or viability, both from a printability and a detectability standpoint. In a commercial environment, good overlay mark detectability may be considered to be a combination of low total measurement uncertainty as well as a short move-acquire-move time, as slow acquisition is detrimental to total throughput for the production line. Modern micro-diffraction-based-overlay targets (μDBO) may be on the order of 10 μm on a side, which provides an inherently low detection signal compared to 40×160 μm2 targets such as those used in the context of monitor substrates.

Additionally, once metrology targets that meet the above criteria have been selected, there is a possibility that detectability will change with respect to process variations, such as film thickness variation, various etch biases, and geometry asymmetries induced by the etch and/or polish processes. Therefore, it may be useful to select a target that has low detectability variation against various process variations. Likewise, the fingerprint (printing characteristics, including, for example, lens aberration) of the specific machine that is to be used to produce the microelectronic device to be imaged will, in general, affect the imaging and production of the metrology targets. It may therefore be useful to ensure that the metrology targets are resistant to fingerprint effects, as some patterns will be more or less affected by a particular lithographic fingerprint.

Figure 6A:
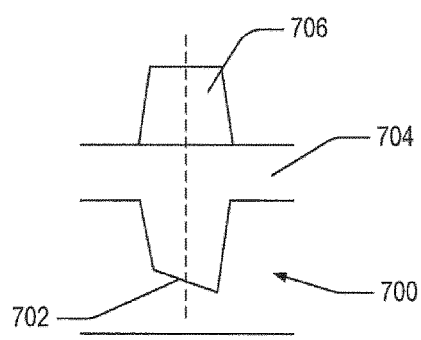
FIGS. 6A and 6B schematically depict a model structure of one period of an overlay target showing an example of variation of the target from ideal, e.g., two types of process-induced asymmetry.
Figure 6B:
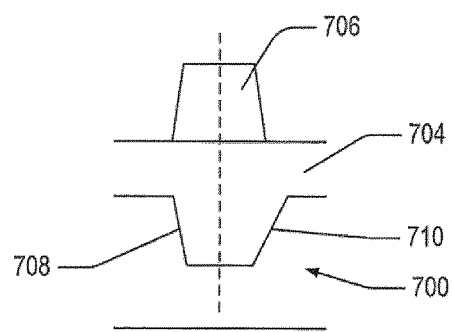

FIGS. 6A and 6Bb schematically show a model structure of one period of an overlay target showing an example of variation of the target from ideal, e.g., two types of process-induced asymmetry. With reference to FIG. 6A, the substrate W is patterned with a bottom grating 700, etched into a substrate layer. The etch process used for the bottom grating results in a tilt of the floor 702 of the etched trench. This floor tilt, FT, can be represented as a structural parameter, for example as a measure of the height drop across the floor 702, in nm. A BARC (bottom anti-reflective coating) layer 704 supports the patterned resist feature of the top grating 706. In this example, the alignment overlay error between the top and bottom grating is zero, as the centers of the top and bottom grating features are at the same lateral position. However, the bottom-layer process-induced asymmetry, i.e. the floor tilt, leads to an error in the measured overlay offset, in this case giving a non-zero overlay offset. FIG. 6B shows another type of bottom-layer process-induced asymmetry that can lead to an error in the measured overlay offset. This may be referred to as side wall angle (SWA) unbalance and is an example of side-wall asymmetry. Features in common with those of FIG. 6A are labeled the same. Here, one side wall 708 of the bottom grating has a different slope to the other side wall 710. This unbalance can be represented as a structural parameter, for example as a ratio of the two side wall angles relative to the plane of the substrate. Both asymmetry parameters floor tilt and SWA unbalance give rise to an apparent overlay error between the top and bottom gratings. This apparent overlay error comes on top of the real overlay error to be measured between the top and bottom gratings.

It is possible to simulate various metrology target designs in order to determine their characteristics.

Figure 7:
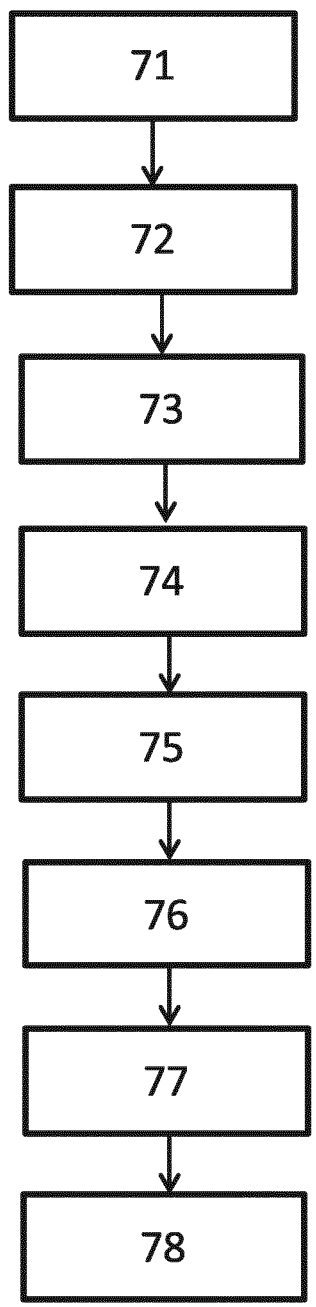
FIG. 7 is an exemplary block diagram illustrating the functional modules of a lithographic simulation model.

In a system for simulating a manufacturing process involving lithography and metrology targets, the major manufacturing system components and/or processes can be described by various functional modules, for example, as illustrated in FIG. 7. Referring to FIG. 7, the functional modules may include a design layout module 71, which defines a metrology target (and/or microelectronic device) design pattern; a patterning device layout module 72, which defines how the patterning device pattern is laid out in polygons based on the target design; a patterning device model module 73, which models the physical properties of the pixilated and continuous-tone patterning device to be utilized during the simulation process; an optical model module 74, which defines the performance of the optical components of the lithography system; a resist model module 75, which defines the performance of the resist being utilized in the given process; a process model module 76, which defines performance of the post-resist development processes (e.g., etch); and metrology module 77, which defines the performance of a metrology system used with the metrology target and thus the performance of the metrology target when used with the metrology system. The results of one or more of the simulation modules, for example, predicted contours and CDs, are provided in a result module 78.

The properties of the illumination and projection optics are captured in the optical model module 74 that includes, but is not limited to, NA-sigma (σ) settings as well as any particular illumination source shape, where σ (or sigma) is outer radial extent of the illuminator. The optical properties of the photo-resist layer coated on a substrate—i.e. refractive index, film thickness, propagation and polarization effects—may also be captured as part of the optical model module 74, whereas the resist model module 75 describes the effects of chemical processes which occur during resist exposure, post exposure bake (PEB) and development, in order to predict, for example, contours of resist features formed on the substrate. The patterning device model module 73 captures how the target design features are laid out in the pattern of the patterning device and may include a representation of detailed physical properties of the patterning device, as described, for example, in U.S. Pat. No. 7,587,704, which is incorporated by reference herein in its entirety. The objective of the simulation is to accurately predict, for example, edge placements and critical dimensions (CDs), which can then be compared against the target design. The target design is generally defined as the pre-OPC patterning device layout, and will be provided in a standardized digital file format such as GDSII or OASIS.

In general, the connection between the optical and the resist model is a simulated aerial image intensity within the resist layer, which arises from the projection of radiation onto the substrate, refraction at the resist interface and multiple reflections in the resist film stack. The radiation intensity distribution (aerial image intensity) is turned into a latent resist image by absorption of photons, which is further modified by diffusion processes and various loading effects. Efficient simulation methods that are fast enough for full-chip applications approximate the realistic 3-dimensional intensity distribution in the resist stack by a 2-dimensional aerial (and resist) image.

Thus, the model formulation describes most, if not all, of the known physics and chemistry of the overall process, and each of the model parameters desirably corresponds to a distinct physical or chemical effect. The model formulation thus sets an upper bound on how well the model can be used to simulate the overall manufacturing process. However, sometimes the model parameters may be inaccurate from measurement and reading errors, and there may be other imperfections in the system. With precise calibration of the model parameters, extremely accurate simulations can be done.

In a manufacturing process, variations in various process parameters have significant impact on the design of a suitable target that can faithfully reflect a device design. Such process parameters include, but are not limited to, side-wall angle (determined by the etching or development process), refractive index (of a device layer or a resist layer), thickness (of a device layer or a resist layer), frequency of incident radiation, etch depth, floor tilt, extinction coefficient for the radiation source, coating asymmetry (for a resist layer or a device layer), variation in erosion during a chemical-mechanical polishing process, and the like.

A metrology target design can be characterized by various parameters such as, for example, target coefficient (TC), stack sensitivity (SS), overlay impact (OV), or the like. Stack sensitivity can be understood as a measurement of how much the intensity of the signal changes as overlay changes because of diffraction between target (e.g., grating) layers. Target coefficient can be understood as a measurement of signal-to-noise ratio for a particular measurement time as a result of variations in photon collection by the measurement system. In an embodiment, the target coefficient can also be thought of as the ratio of stack sensitivity to photon noise; that is, the signal (i.e., the stack sensitivity) may be divided by a measurement of the photon noise to determine the target coefficient. Overlay impact measures the change in overlay error as a function of target design.

It has been found that the effects of process perturbations is significantly linear to the amount of perturbation, particularly for, for example, etch side wall angle, a common variation across a substrate. This finding allows for simulation once for each perturbation parameter, and a sensitivity can be calculated for the parameter. When the variation amount is different or there are multiple variations, the effect on a metrology target can simply be linearly scaled or summed Where the variations are large enough to enter the non-linear domain, it may be that the linear sensitivities may remain good indicators of the non-linear performance, and are sufficient for ranking targets in terms of process robustness. Thus, in an embodiment, reduced simulation and faster evaluation of suitable targets may be accomplished. For example, one simulation may be performed per perturbation parameter, and other perturbation amounts and combinations can be added linearly.

It has been found that variation of a metrology target parameter, par, can be considered to be linearly dependent on variation of one or more process parameters, ppar, and can be expressed for one or more different process parameters, ppar, as:

$$\partial par = \Sigma_{ppar} \Delta ppar \cdot \frac{\partial par}{\partial ppar} \qquad (1)$$

where the term $$\frac{\partial par}{\partial ppar}$$

is the sensitivity of the metrology target parameter par to a particular process parameter ppar. Further, it has been discovered that the sensitivity of a metrology target parameter, par, to a process parameter, ppar, for creating the metrology target is generally independent of other process parameters within the range of process perturbations. Accordingly, it is possible to determine the sensitivity term $$\frac{\partial par}{\partial ppar}$$

for each of the process parameters independently and use those sensitivities for different process parameter values and/or different process parameter profiles (e.g., different combinations of process parameters). In an embodiment, the sensitivity of the metrology target parameter to a particular process parameter is considered to be linear within the design range of the process variations in the manufacturing process. Thus, the impact of variation of a plurality of process parameters to a metrology target parameter may be determined using the summation of the product of the sensitivity and its respective process parameter variation for the plurality of process parameters using, e.g., equation (1).

In an embodiment, the metrology target parameter may be stack sensitivity, target coefficient, overlay error, etc. In an embodiment, the process parameters may be any parameters characterizing the target post-exposure and/or before use for metrology. In an embodiment, the process parameters may be a parameter characterizing the physical formation of the metrology target and/or the use of the metrology target for metrology. In an embodiment, the process parameter may any one selected from: side wall angle of the metrology target, material thickness of the metrology target, material relative permittivity, material refractive index, metrology radiation wavelength, an etch parameter (e.g., etch depth, etch type, etc.), floor tilt, extinction coefficient, coating asymmetry, chemical-mechanical polish erosion, etc.

In various embodiments, the sensitivity of the one or more parameters may be measured or simulated. For example, one or more process variations can be measured. For example, a technique such as scatterometry and/or ellipsometry can measure a thin film's refractive index, relative permittivity, thickness, etc. An atomic force microscope and/or a cross section scanning electron microscope can examine and measure a structure's profile, for example side wall angle, width of a trench, depth of a trench, etc. Accordingly, experiments can be designed where essentially only one process parameter is varying predominately and is measured, and one or more metrology target parameters with and without the variance can also be measured by a metrology tool (e.g., a scatterometer). Sensitivity can then be calculated by taking the ratio of the observed metrology target parameter change over the process parameter change. Because the magnitude of change is comparable to measurement uncertainty, a large number of measurements may be needed to establish statistical correlation between measured and simulated sensitivities. For example, in an embodiment, process parameter perturbation experiments (a subset of which are sometimes referred to as meander experiments) may be performed to determine the sensitivity. As an example, during substrate processing, the process may be slightly varied, causing a variation in a process parameter. This may cause, for example, measurable overlay error in product patterns as well as in metrology targets. The process parameter can be measured or determined by a sensor and the parameter of interest (e.g., overlay) can also be measured or determined. Thus sensitivity of the parameter (e.g., overlay) to the process parameter can be calculated. Similarly, the sensitivity may be simulated using a lithographic model (e.g., one or more of modules 71-75) and a metrology model. For example, a simulation may be performed by using a lithography model for the pertinent process parameter where the process parameter is varied for a certain amount (e.g., several nm or a certain small percentage (e.g., 1-5%) to get a profile and the profile is provided to a metrology simulation to give a variation of an applicable parameter, e.g., overlay for variation in the process parameter and thus yield a sensitivity.

As described above, process parameters, such as side-wall angle unbalance, can be obtained by measurement or simulation. However, measurements can be destructive and/or slow. This is the case for example where a cross section scanning electron microscope (SEM) is used to determine side-wall angle unbalance. Simulation tends not to be destructive but can be complex (and therefore slow or unreliable).

The present inventors have recognized that performing measurements of overlay error that have different sensitivities to perturbations in a process parameter can provide a convenient and efficient measurement of the perturbations themselves, independently of the actual overlay error.

Figure 8:
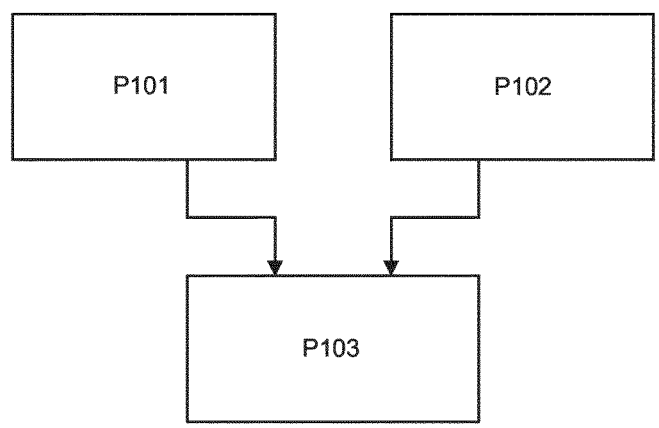
FIG. 8 illustrates the framework of an example method for measuring process parameters.

FIG. 8 illustrates the framework of an example method for measuring process parameters in this way. In a first step, P101, a first measurement of overlay error is made. In a second step, P102, a second measurement of overlay error is made. The first and second measurements of overlay error are different. For example, the first and second measurements may use different metrology targets and/or different measurements modes. This is discussed in further detail below. In a third step, P103, a measure of the process parameter is obtained based on the first and second measurements obtained in steps P101 and P102. This is made possible because the first measurement of overlay error is designed to be more sensitive to a perturbation in the process parameter than the second measurement of overlay error by a known amount. The sensitivity is a measure of the extent to which a perturbation in the process parameter affects (e.g. causes a deviation or error in) the overlay error measurement. The sensitivity may be expressed as the rate of change of the output of the overlay error measurement with respect to the process parameter.

Denoting the output of the first measurement of overlay error as OV1, and the output of the second measurement of overlay error as OV2, the sensitivity of the first measurement of overlay error to perturbations in a process parameter A may be expressed as $$\frac{\partial OV1}{\partial A}$$

and sensitivity of the second measurement of overlay error to perturbations in the process parameter A may be expressed as $$\frac{\partial OV2}{\partial A}.$$

In this case, the difference between the measured overlay errors, OV2−OV1, can be used to provide a measure of the process parameter A via the following expression:

$$OV2 - OV1 = A \cdot \frac{\partial OV2}{\partial A} - A \cdot \frac{\partial OV1}{\partial A} = A \cdot \left(\frac{\partial OV2}{\partial A} - \frac{\partial OV1}{\partial A}\right)$$

Thus, a measure of the process parameter A can be obtained by measuring the difference in overlay error, OV2−OV1, and dividing this difference by the difference in sensitivities to a perturbation in the process parameter of the overlay error measurements. The difference in sensitivities, $$\frac{\partial OV2}{\partial A} - \frac{\partial OV1}{\partial A},$$

can be determined beforehand by measurements (for example by applying the same measurement of overlay error to measurements of a metrology target under a range of different values of the process parameter in question) or by computer simulation.

Thus, a method is provided in which overlay error measurements can be used to obtain a measure of a process parameter, such as side-wall angle unbalance, that can be difficult, time-consuming and/or destructive to obtain via a separate measurement (such as cross section SEM).

In an embodiment, the first and second measurements of overlay error are arranged such that the sensitivity to perturbations of the process parameter of the second measurement of overlay error is much greater (for example more than 5 times greater, preferably more than 10 times greater, preferably more than 20 times greater, preferably more than 100 times greater) than the sensitivity to perturbations of the process parameter of the first measurement of overlay error. In this scenario, the measure of the process parameter may be approximated by $$A = (OV2 - OV1)/\frac{\partial OV2}{\partial A}$$

In an embodiment, the sensitivity to perturbations of the process parameter of the first measurement of overlay error is arranged to be substantially zero (e.g. is optimized to minimize sensitivity to the greatest extent possible).

In an embodiment, the first and second measurements of overlay error are performed using two different target structures (e.g. metrology targets). In such an embodiment, the method of measuring the target structures may be the same in each case. For example, where the measuring involves applying radiation to the target structures (e.g. scatterometry or ellipsometry), the properties of the applied radiation may be the same in each case (e.g. the same direction of incidence, the same wavelength or range of wavelengths, and/or the same polarization characteristics). Furthermore, the way in which the radiation is detected and/or analyzed may be the same. However, the target structures themselves are designed (or selected) to cause the measurements of overlay using the different target structures to have different sensitivities to the process parameter of interest. The target structures may be designed using computer simulation as described above. In an embodiment, one or more suitable target structures are selected based on simulations using a large number of different target structures and/or ways of inspecting the target structures.

Figure 9:
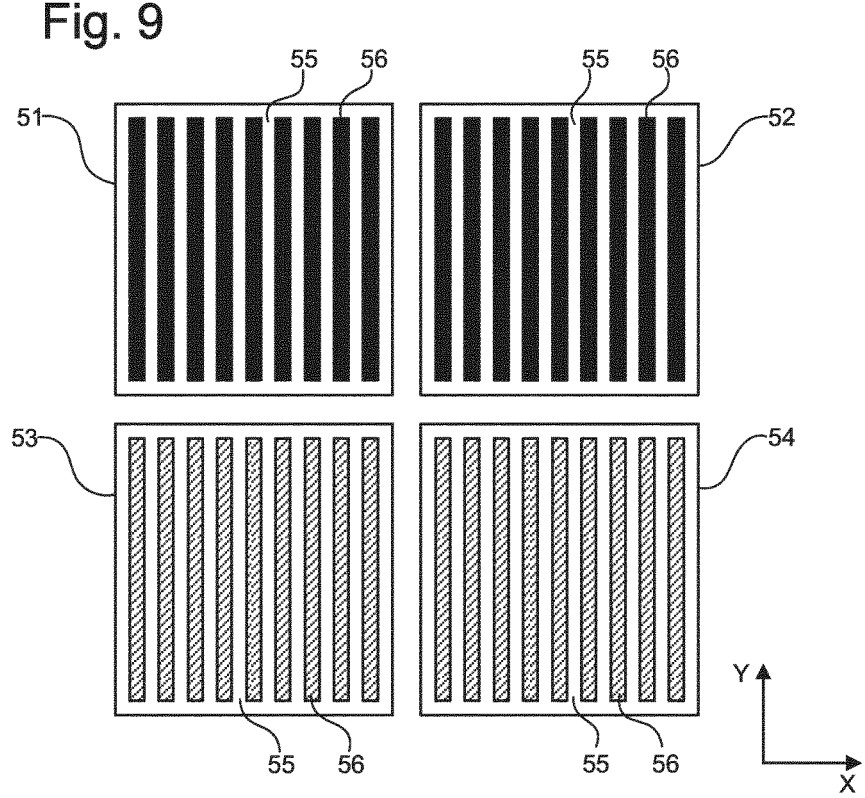
FIG. 9 illustrates example first and second target structures for use in the method of FIG. 8.

FIG. 9 illustrates example first and second target structures. In this example, the first target structure comprises two line gratings 51 and 52. The second target structure comprises two line gratings 53 and 54. The first target structure 51,52 is configured such that a measurement of overlay error using the first target structure 51,52 is more sensitive to a perturbation in a process parameter or parameters of interest than would be a measurement of overlay error using the second target structure 53,54.

In other embodiments, the first target structure and/or the second target structure may comprise other types of feature or periodic structure and/or more than two or less than two line gratings. The line gratings 51-54 are composite line gratings comprising grating patterns in two different layers. FIG. 9 is a top view and illustrates only the grating pattern formed in an upper layer. The line gratings 51-54 comprise areas corresponding to line features 56 (where line features will be formed after development or etching) and areas corresponding to trench features 55 (where trenches will be formed after development or etching). A lower layer, covered by the upper layer, comprises a grating pattern that has been fully formed, for example by etching trenches in a material. The grating pattern in the upper layer is not necessarily yet fully formed. The grating pattern in the upper layer may for example be a latent image (i.e. an image defined by a resist immediately after exposure in a lithographic process). Alternatively, the grating pattern in the upper layer may be semi-latest image (e.g. an image defined by a resist after exposure and after a post-exposure bake step). Alternatively, the grating pattern in the upper layer may be defined after removal of material during development or etching of the layer.

Computer simulation may be used to design metrology targets having the desired sensitivities. For example, a computer simulation may be used to design a large number of targets having desired overlay measurement characteristics for the application in question. A smaller number of targets satisfying the requirements of sensitivity to the process parameter of interest may then be selected from the set of targets.

In an illustrative example, the inventors simulated a large number of targets comprising composite gratings having a pitch between 500-600 nm, and with critical dimension (CD) variations in both of the two layers of the gratings. From these simulated targets, the following two were selected:

Target 1: line-on-line type (having lines of the grating in one layer aligning with the lines of the grating in the other layer), pitch=500 nm, bottom layer CD=225 nm, top layer CD 255 nm, target coefficient (TC)=0.049.

Target 2: line-on-trench type (having lines of the grating in one layer aligning with the trenches of the grating in the other layer), pitch=560 nm, bottom layer CD=275 nm, top layer CD=275 nm, target coefficient (TC)=0.088.

A target coefficient (TC) of below 0.1 is considered to be very well measurable. The simulations indicated that the measured overlay error for the case of zero overlay error and SWA unbalance=1 degree was 0.01 nm for target 1 and 1.01 for target 2. Thus, each 1 degree in SWA unbalance corresponds to about 1 nm in overlay error difference between the two targets. If the measurement repeatability of the overlay error difference is about 0.2 nm, this means that the measurement repeatability of the SWA unbalance is about 0.2 degrees.

In an embodiment, the first and second measurements of overlay error measure overlay error parallel to a first line (e.g. the X axis). In this case, the process parameter may comprise a parameter that is defined relative to the first line. For example, the process parameter may comprise an asymmetry of a feature when viewed along a direction perpendicular to the line (e.g. SWA unbalance of grating lines running perpendicular to the first line). In such an embodiment, the method may further comprise third and fourth measurements of overlay error that measure overlay error parallel to a second line that is at a non-zero angle relative to the first line (e.g. the Y axis, perpendicular to the X axis). The process parameter may further comprise a parameter that is defined relative to the second line (e.g. SWA unbalance of grating lines running perpendicular to the second line).

In the embodiment shown in FIG. 9, the grating lines are perpendicular to the X axis and are therefore suitable for measuring overlay errors parallel to the X axis. In the same way as described above with reference to FIG. 5, the gratings may be provided with different biases. For example, gratings 51 and 53 may be provided with a+d bias and gratings 52 and 54 may be provided with a−d bias. In other embodiments, further composite gratings may be provided to improve accuracy, with different combinations of biases.

For example, a 3×3 array of nine composite gratings having biases −4d, −3d, −2d, −d, 0, +d, +2d, +3d, +4d, as discussed above, may be used.

In other embodiments, the target structures may be oriented differently so as to measure overlay parallel to other directions. In other embodiments, target structures that are configured to measure overlay errors in two or more different directions are provided. For example, a set of target structures of the type illustrated in FIG. 9 may be provided in combination with a similar set of target structures that are rotated by 90 degrees relative thereto (or by any other angle). Such a combination of sets of target structures may be configured independently to measure overlay errors parallel to different directions.

In an embodiment, the target structures are micro-diffraction-based-overlay targets (μDBO). Such targets are small enough to allow the targets to be provided both within a die (amongst device features) and in scribe lines between dies.

In the above embodiments the first and second measurements of overlay error are performed using different target structures. However, this is not essential. In other embodiments the first and second measurements of overlay error may be performed using the same target structure or structures but different measurement techniques. The different measurement techniques are chosen such that the first measurement of overlay error is more sensitive to a perturbation in the process parameter of interest than the second measurement of overlay error by a known amount. For example, where first and second measurements of overlay error involve the application of radiation to the target structures (e.g. in scatterometry or ellipsometry), the properties of the applied radiation may be different (e.g. the direction of incidence may be different, the wavelength or range of wavelengths applied may be different, and/or the polarization characteristics may be different). Alternatively or additionally, the way in which the radiation is detected and/or analyzed may be different.

Using different target structures and the same measurement technique may facilitate rapid measurement and thus throughput. Using different measurement techniques to measure the same metrology target may reduce the number of target structures that are needed.

The first and second measurements of overlay error may be performed at a plurality of different locations on the substrate, for example by providing appropriate target structures at a corresponding plurality of locations on the substrate. This allows the process parameter or process parameters of interest to be determined accurately even in the case where the process parameter varies significantly as a function of position on the substrate.

According to an embodiment, the process parameter being measured is an asymmetry of a feature of a target structure. The feature asymmetry may for example comprise an asymmetry in the cross-sectional shape of a line or trench in a line grating of the target structures. The asymmetry may for example comprise an asymmetry with respect to a mirror plane cutting through the center of the line or trench when viewed along the line or trench, and extending perpendicular to the plane of the grating. The feature asymmetry may comprise an asymmetry in the angles of side-walls defining a line in the line grating (e.g. where the magnitude of an angle of the side wall relative to a normal to the plane of the grating is different for side walls on opposite sides of a line). This has been referred to above as SWA unbalance, and is discussed with reference to FIG. 6B. The feature asymmetry may relate to a feature in either or both of the upper and lower layers of a composite grating, although where walls of the feature are formed by developing an exposed resist or by etching this may often apply only to the lower layer where this is the only layer that has been treated in this way. However, the method may also be applied to composite gratings where more than one of the layers has been subjected to post-exposure development or etching.

The asymmetry in the cross-sectional shape of a line or trench may comprise a tilt in the floor of the trenches between lines of the line grating. This geometry has been discussed above with reference to FIG. 6A. The asymmetry in the cross-sectional shape of a line or trench may also comprise a combination of the side-wall angle unbalance and tilt. The asymmetry may additionally or alternatively include other factors such as curvature of the side-walls and/or trench floors.

Thus, the process parameter measured by an embodiment may comprise one or more of the following: an asymmetry in a feature of a metrology target, an asymmetry in the cross-sectional shape of a line or trench in a line grating of a target structure, an asymmetry in the angle of side-walls defining a line in a line grating of a target structure.

Additionally or alternatively, the measured process parameter may comprise a variation from a reference value of one or more of the following: etch depth of a feature formed on the substrate, thickness of a layer or feature formed on the substrate, relative permittivity of material forming a layer or feature on the substrate, refractive index of material formed a layer or feature on the substrate.

Figure 10:
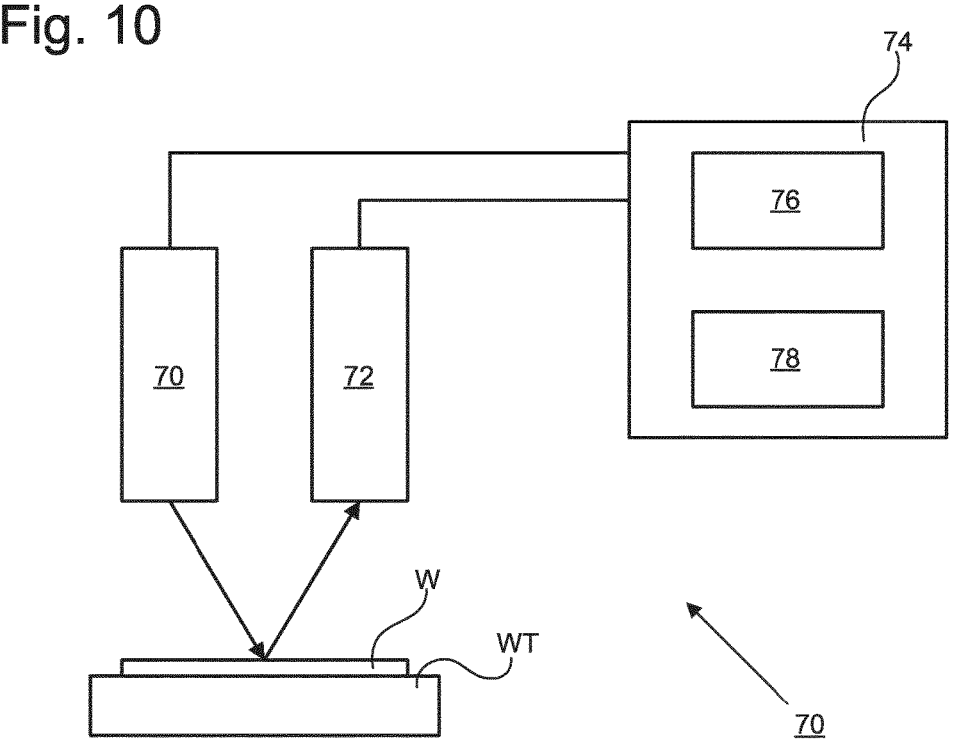
FIG. 10 illustrates an example apparatus for measuring a process parameter.

FIG. 10 illustrates an inspection apparatus 71 adapted to measure a process parameter, for example using one or more of any of the methods described above. The apparatus 71 comprises an optical system 71 (comprising for example a radiation source and optics for directing an output from the radiation source) arranged to direct radiation onto a substrate W (e.g. onto one or more target structures on the substrate W). A detector 72 is arranged to detect radiation after interaction (e.g. scattering, reflection, etc.) between the radiation and the substrate (e.g. between the radiation and one or more of the metrology targets). The optical system 71 and detector 72 are controlled by a processing unit 74. The processing unit 74 comprises an overlay error processing module 76 arranged to obtain a measure of overlay error by analyzing an output from the detector 72. The processing unit 74 further comprises a process parameter obtaining module 78 arranged to obtain a measure of the process parameter of interest by causing the optical system 71, detector 72 and overlay error processing module 76 to perform the following steps. Firstly, first and second measurements of overlay error in a region on a substrate are performed (e.g. based on the interaction between the radiation from the optical system 71 and the substrate, detected by the detector 72). Secondly, a measure of the process parameter is obtained, based on the first and second measurements of overlay error, the first measurement of overlay error being designed, as in the example methods discussed above, to be more sensitive to a perturbation in the process parameter than the second measurement of overlay error by a known amount.

In an embodiment, the inspection apparatus 70 forms part of a lithographic system. The lithographic system comprises an illumination system arranged to illuminate a pattern, a projection system PS arranged to project an image of the pattern onto a substrate W, and the inspection apparatus 70. The lithographic apparatus may be configured to use one or more process parameters measured by the inspection apparatus in applying the pattern to the substrate or further substrates. For example, the lithographic apparatus may be configured to make adaptations to improve the process parameter. For example, where the process parameter represents an error the lithographic apparatus may make adaptations to reduce the size of the error. Where the process parameter is a measure of side-wall angle unbalance the lithographic apparatus may make adaptations to reduce the unbalance.

A method of manufacturing devices may be provided that makes use of the methods of measuring a process parameter described above. The method may include measuring a process parameter by inspecting one or more target structures formed as part of a device pattern or in a region beside a device pattern (e.g. in scribe lines). The method may include controlling the lithographic process for later patterned regions of the same substrate or for later substrates in accordance with the results of the measuring of the process parameter (e.g. to improve or correct the process parameter as described above).

The example target structures described herein are metrology targets specifically designed and formed for the purposes of measurement. In other embodiments, properties may be measured on targets which are functional parts of devices formed on the substrate. Many devices have regular, grating-like structures. The terms 'target', 'target grating' and 'target structure' as used herein do not require that the structure has been provided specifically for the measurement being performed.

While overlay targets in the form of gratings have been described, in an embodiment, other target types may be used such as box-in-box image based overlay targets.

While metrology targets to determine overlay have been primarily described, the metrology targets may be used to determine, in the alternative or additionally, one of more other characteristics, such as focus, dose, etc.

In association with the physical grating structures of the targets as realized on substrates and patterning devices, an embodiment may include a computer program containing one or more sequences of machine-readable instructions describing a method of designing a target, producing a target on a substrate, measuring a target on a substrate and/or analyzing measurements to obtain information about a lithographic process. This computer program may be executed for example within unit PU in the apparatus of FIGS. 3 and 4 and/or the control unit LACU of FIG. 2. There may also be provided a data storage medium (e.g., semiconductor memory, magnetic or optical disk) having such a computer program stored therein. Where an existing apparatus, for example of the type shown in FIGS. 1-4, is already in production and/or in use, an embodiment can be implemented by the provision of updated computer program products for causing a processor of the apparatus to perform a method as described herein.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So the controller(s) may operate according the machine readable instructions of one or more computer programs.

Although specific reference may have been made above to the use of embodiments in the context of optical lithography, it will be appreciated that an embodiment of the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further, although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The descriptions above are intended to be illustrative, not limiting. Thus, it will be apparent to one skilled in the art that modifications may be made to the invention as described without departing from the scope of the claims set out below. For example, one or more aspects of one or more embodiments may be combined with or substituted for one or more aspects of one or more other embodiments as appropriate. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance. The breadth and scope of the invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of measuring a process parameter for a manufacturing process involving lithography, comprising:
   performing first and second measurements of overlay error in a region on a substrate using respective first and second target structures; and
   obtaining a measure of the process parameter based on the first and second measurements of overlay error,
   wherein the first and second target structures are configured such that the first measurement of overlay error is more sensitive to a perturbation in the process parameter than the second measurement of overlay error by a known amount.

2. The method according to claim 1, wherein the process parameter comprises an asymmetry in a feature of a target structure formed on the substrate by a lithographic process.

3. The method according to claim 2, wherein the asymmetry in a feature comprises an asymmetry in the cross-sectional shape of a line or trench in a line grating of the target structure, the asymmetry being defined with respect to a mirror plane cutting through the center of the line or trench when viewed along the line or trench, and extending perpendicular to the plane of the grating.

4. The method according to claim 3, wherein the asymmetry in a feature comprises an asymmetry in the angles of side-walls defining a line in the line grating relative to a normal to the plane of the grating.

5. The method according to claim 3, wherein the asymmetry in a feature comprises a tilt in the floor of a trench formed between lines of the line grating.

6. The method according to claim 1, wherein simulation of the first and second measurements of overlay error is used to design the first measurement of overlay error to be more sensitive to a perturbation in the process parameter than the second measurement of overlay by a known amount.

7. The method according to claim 1, wherein:
   the first and second measurements of overlay error use radiation having first wavelength characteristics and first polarization characteristics to measure the overlay error of the first and second target structures, respectively.

8. The method according to claim 1, wherein the first and second target structures each comprise a line grating.

9. The method according to claim 1, wherein the process parameter comprises a variation from a reference value of one or more of the following: etch depth of a feature formed on the substrate, thickness of a layer or feature formed on the substrate, relative permittivity of material forming a layer or feature on the substrate, refractive index of material forming a layer or feature on the substrate.

10. A non-transitory computer readable product comprising machine-readable instructions for causing a processor to perform the operations step of comprising:
    performing first and second measurements of overlay error in a region on a substrate using respective first and second target structures; and
    obtaining a measure of the process parameter based on the first and second measurements of overlay error,
    wherein the first and second target structures are configured such that the first measurement of overlay error is more sensitive to a perturbation in the process parameter than the second measurement of overlay error by a known amount.

11. An inspection apparatus for measuring a process parameter for a manufacturing process involving lithography, comprising:
    an optical system arranged to direct radiation onto a substrate;
    a detector arranged to detect radiation after interaction between the radiation and the substrate;
    an overlay error processing module arranged to obtain a measure of overlay error by analyzing an output from the detector; and
    a process parameter obtaining module arranged to obtain a measure of the process parameter by causing the optical system, detector and overlay error processing module to:
       perform first and second measurements of overlay error in a region on the substrate using respective first and second target structures; and
       obtain a measure of the process parameter based on the first and second measurements of overlay error, wherein
       the first and second target structures are configured such that the first measurement of overlay error is more sensitive to a perturbation in the process parameter than the second measurement of overlay error by a known amount.

12. A lithographic system comprising:
a lithographic apparatus comprising:
- an illumination system arranged to illuminate a pattern;
- a projection optical system arranged to project an image of the pattern onto a substrate; and an inspection apparatus comprising,
- an optical system arranged to direct radiation onto a substrate;
- a detector arranged to detect radiation after interaction between the radiation and the substrate;
- an overlay error processing module arranged to obtain a measure of overlay error by analyzing an output from the detector; and
- a process parameter obtaining module arranged to obtain a measure of the process parameter by causing the optical system, detector and overlay error processing module to:
  - perform first and second measurements of overlay error in a region on the substrate using respective first and second target structures; and
  - obtain a measure of the process parameter based on the first and second measurements of overlay error, wherein
  the first and second target structures are configured such that the first measurement of overlay error is more sensitive to a perturbation in the process parameter than the second measurement of overlay error by a known amount;

wherein the lithographic apparatus is arranged to use one or more process parameters measured by the inspection apparatus in applying the pattern to the substrate or further substrates.

13. A method of manufacturing devices wherein a device pattern is applied to a series of substrates using a lithographic process, the method comprising:
- measuring a process parameter by inspecting first and second target structures formed as part of or beside the device pattern on at least one of the substrates using a method comprising,
  - performing first and second measurements of overlay error in a region on a substrate using respective first and second target structures; and
  - obtaining a measure of the process parameter based on the first and second measurements of overlay error,
  wherein the first and second target structures are configured such that the first measurement of overlay error is more sensitive to a perturbation in the process parameter than the second measurement of overlay error by a known amount; and
- controlling the lithographic process for later substrates in accordance with the result of the measuring of the process parameter.

* * * * *